United States Patent [19]

Grey

[11] Patent Number: 5,091,543
[45] Date of Patent: Feb. 25, 1992

[54] PREPARATION OF CYCLIC CARBONATES USING ALKYLAMMONIUM AND TERTIARY AMINE CATALYSTS

[75] Inventor: Roger A. Grey, West Chester, Pa.

[73] Assignee: Arco Chemical Technology, Inc., Wilmington, Del.

[21] Appl. No.: 597,978

[22] Filed: Oct. 15, 1990

[51] Int. Cl.$^5$ .......................................... C07D 317/12
[52] U.S. Cl. .................. 549/228; 549/229; 549/230
[58] Field of Search .................. 549/228, 229, 230

[56] References Cited

U.S. PATENT DOCUMENTS

| | | | |
|---|---|---|---|
| 2,773,070 | 12/1956 | Lichtenwalter et al. | 260/340.2 |
| 3,426,042 | 2/1969 | Hostettler et al. | 260/340.2 |
| 3,663,569 | 5/1972 | Lew | 260/340.2 |
| 4,181,676 | 1/1980 | Buysch et al. | 260/463 |
| 4,314,945 | 2/1982 | McMullen et al. | 549/229 |
| 4,325,874 | 4/1982 | Jacobson | 549/230 |
| 4,344,881 | 8/1982 | Strege et al. | 549/229 |
| 4,353,831 | 10/1982 | Strege et al. | 549/229 |
| 4,440,937 | 4/1984 | Krimm et al. | 549/228 |
| 4,824,969 | 4/1989 | Austin et al. | 549/230 |
| 4,835,289 | 5/1989 | Brindöpke | 549/230 |
| 4,877,886 | 10/1989 | Ream | 549/230 |
| 4,892,954 | 1/1990 | Brindöpke et al. | 549/230 |
| 4,931,571 | 6/1990 | Weinstein | 549/230 |
| 5,003,084 | 3/1991 | Su et al. | 549/230 |

OTHER PUBLICATIONS

Ind. and Eng. Chem. 50 (1958) 767.
J. Am. Chem. Soc. 68 (1946) 781.
J. Am. Chem. Soc. 80 (1958) 4596.
Venturello et al, CA 103-104873y (1985).
Kim et al, CA 106-156323a (1987).
Akgun et al, CA 106-84432k (1987).
Baba et al, CA 108-37691a (1988).
Mizuno et al, CA 112-76357y (1990).

*Primary Examiner*—Cecilia Shen
*Attorney, Agent, or Firm*—Jonathan L. Schuchardt

[57] ABSTRACT

A method of preparing five- and six-membered cyclic carbonates is disclosed. The process comprises reacting a 1,2- or 1,3-diol with an acyclic diester of carbonic acid in the presence of a catalyst selected from alkylammonium salts, tertiary amines, and ion-exchange resins containing alkylammonium or tertiary amino groups. Cyclic carbonates free of polycarbonate by-products are obtained in high yields.

31 Claims, No Drawings

PREPARATION OF CYCLIC CARBONATES USING ALKYLAMMONIUM AND TERTIARY AMINE CATALYSTS

FIELD OF THE INVENTION

This invention relates to the synthesis of cyclic carbonates. A method of preparing cyclic carbonates from diesters of carbonic acid is disclosed. Cyclic carbonates are useful as solvents, chemical intermediates, and monomers for polycarbonate synthesis.

BACKGROUND OF THE INVENTION

Cyclic carbonates, cyclic esters of carbonic acid, have been prepared by many well-known methods. The reaction of ethylene glycol with phosgene to produce ethylene carbonate, the simplest of the cyclic esters, is more than a century old (*J. prakt. Chem.* 28 (2) 439 (1883)). Because of the extreme toxicity and corrosivity of phosgene, alternative routes to cyclic carbonates have been explored.

U.S. Pat. No. 1,907,891 teaches the preparation of cyclic carbonates from sodium bicarbonate and alkylene halohydrins.

U.S. Pat. Nos. 4,181,676 and 3,642,858, and German Patent 2,615,665 teach base-catalyzed preparation of acyclic dialkyl carbonates from cyclic carbonates. Japanese Kokai 88-238,043 teaches the same reaction catalyzed by anion exchange resins having quaternary ammonium groups.

Synthetic approaches to commercially interesting cyclic carbonates, especially ethylene carbonate and propylene carbonate, have focused on the reaction between an epoxide and carbon dioxide, a reaction first disclosed in German Patent 740,366 (1943). The process has been improved substantially by the use of various catalysts, including tetraalkylammonium halides (U.S. Pat. No. 2,773,070) and quaternary ammonium bases (U.S. Pat. No. 2,667,497). Some of this work is summarized in W. J. Peppel, *Ind. Eng. Chem.* 50 (1958) 767. The epoxide/$CO_2$ reaction has been catalyzed by other additives, including anion exchange resins (U.S. Pat. No. 4,233,221), amines (U.S. Pat. No. 2,773,881), and quaternary ammonium hydroxides, carbonates or bicarbonates (U.S. Pat. No. 2,873,282).

Recent cyclic carbonate syntheses include reaction of a diol with an alkyl trichloroacetate in the presence of base (U.S. Pat. No. 4,344,881), thermal decomposition of halogenated aliphatic carbonates (U.S. Pat. No. 4,332,729), reaction of a 1,2-diol with chlorosulfonyl isocyanate (*Synth. Commun.* 18 (1988) 2295), reaction of tertiary 1,2-diols with acetic anhydride and 4-dimethylaminopyridine (*J. Org. Chem.* 49 (1984) 3974), and reaction of a diol with di-2-pyridyl carbonate (*Heterocycles* 24 (1986) 1625).

Transesterification of acyclic diesters of carbonic acid with glycols in the presence of an alkaline catalyst to give cyclic carbonates is described by M. Morgan and L. Cretcher (*J. Am. Chem. Soc.* 68 (1946) 781). Preparation of ethylene carbonate from ethylene glycol and diethyl carbonate in the presence of potassium carbonate is described. U S. Pat. No. 2,441,298 teaches the preparation of ethylene carbonate from ethylene glycol and diethyl carbonate using metallic sodium as the catalyst. The use of sodium methoxide as the alkaline catalyst for making 6-membered cyclic carbonates is illustrated by Sarel and Pohoryles (*J. Am. Chem. Soc.* 80 (1958) 4596). Dialkyltin oxides are described as transesterification catalysts in U.S. Pat. No. 3,663,569. Other compounds known to catalyze the transesterification reaction between acyclic diesters of carbonic acid and diols, typically bases and transition metal compounds, are outlined in U.S. Pat. Nos. 4,440,937 and 3,426,042. These include, among other catalysts, oxides, hydroxides, alcoholates, carboxylates, and carbonates of sodium, potassium, aluminum, thallium, and lead, as well as various titanium compounds, metal chelates, and manganese salts.

A disadvantage of basic and transition metal transesterification catalysts is that they often catalyze the polymerization of cyclic carbonates, especially cyclic carbonates having 6-membered rings. Consequently, the use of these catalysts often results in product mixtures that contain unwanted polycarbonate polymers in addition to the desired cyclic carbonates. A transesterification process that gives cyclic carbonates free from polycarbonate by-products is needed.

SUMMARY OF THE INVENTION

This invention provides a process for preparing a cyclic carbonate. The process comprises reacting a 1,2- or 1,3-diol with a diester of carbonic acid in the presence of a catalyst selected from alkylammonium salts, pyridinium salts, tertiary amines, and strong or weak-base ion-exchange resins containing active groups selected from alkylammonium or tertiary amino, at a temperature and for a time sufficient to form the cyclic carbonate. The cyclic carbonate is obtained in high yield and is substantially free of polycarbonate by-products. The reaction can be used to prepare cyclic carbonates having 5 or 6-membered rings.

DETAILED DESCRIPTION OF THE INVENTION

According to the process of the invention, cyclic carbonates having five or six-membered rings are prepared from the reaction of 1,2- or 1,3-diols and esters of carbonic acid.

Diols useful in the process of the invention have the general formulae:

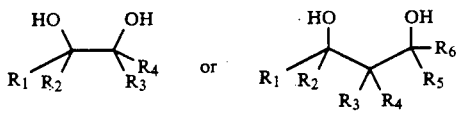

wherein $R_1$ through $R_6$, which may be the same or different, are selected from linear, branched, or cyclic $C_1$–$C_{30}$ alkyl, hydroxyalkyl, aryl, or aralkyl groups. Any pair of R groups can also be part of a ring, for example:

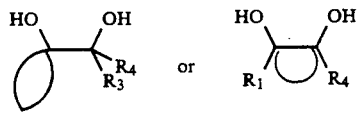

Examples of suitable diols that can be used in the process of the invention include, but are not limited to, ethylene glycol, propylene glycol, 1,3-propanediol, 2-methyl 1,3-propanediol, 2,2-dimethyl-1,3-propanediol, trans-1,2-cyclohexanediol, cis-1,3-cyclohexanediol, 1-hydroxy-1-hydroxymethylcyclohexane, 2-cyclopentyl-1,3-propanediol, 2,2-diphenyl-1,3-propanediol, 2,2-dibenzyl-1,3-propanediol, 2,3- butanediol, pinacol, and the like, and mixtures thereof. Preferably, the diol is ethylene glycol or propyene glycol. Polyhydroxy aliphatic compounds that have 3 or more hydroxyl groups may also be used, provided that at least two of the hydroxyl groups comprise a 1,2- or 1,3-diol moiety. Examples of such polyhydroxy aliphatic compounds include, but are not limited to, pentaerythritol, glycerin, trimethylolpropane, sucrose, and the like, and mixtures thereof. Compounds that have 4 or more hydroxyl groups, such as pentaerythritol, may be able to form 2 or more cyclic carbonate moieties in the same molecule via the process of the invention.

Diesters of carbonic acid are a second necessary reactant in the process of the invention. The diesters have the general formula:

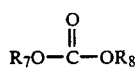

wherein $R_7$ and $R_8$, which may be the same or different, represent alkyl, aryl, or aralkyl groups.

Examples of suitable diesters of carbonic acid that may be used include, but are not limited to, dimethyl carbonate, diethyl carbonate, diphenyl carbonate, methyl ethyl carbonate, methyl phenyl carbonate, methyl benzyl carbonate, di-n-butyl carbonate, and the like, and mixtures thereof. Preferably, $R_7$ and $R_8$ are the same. Preferred carbonate esters are dimethyl carbonate, diethyl carbonate, and diphenyl carbonate.

Alkylammonium or pyridinium salts are used in the process of the invention to catalyze the reaction between the diester of carbonic acid and the diol. The alkylammonium salts are represented in general by the formula:

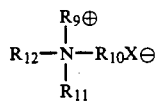

wherein $R_9$ to $R_{12}$, which may be the same or different, are selected from hydrogen, hydroxyalkyl, alkyl, aryl, and aralkyl. Only one of the R groups may be hydrogen. The alkyl and aralkyl groups may be linear, branched, or cyclic, and may contain from 1 to 30 carbon atoms. The counterion, X-, is a monovalent anion selected from the group consisting of halide, hydroxide, alkoxide, carbonate, bicarbonate, dihydrogen phosphate, and bisulfate.

Examples of suitable alkylammonium or pyridinium salts that may be employed include, but are not limited to, tetra-n-butylammonium bromide, tri-n-butylamine hydrochloride, tetra-n-butylammonium dihydrogen phosphate, trimethylammonium iodide, trimethylamine hydrochloride, trimethylbenzylammonium chloride, tetraoctylammonium bromide, tetra-n-butylammonium hydroxide, tetra-n-butylammonium hydrogen sulfate, pyridinium methyl iodide, pyridine hydrochloride, trimethyl-(2-hydroxyethyl)ammonium chloride, and the like, and mixtures thereof.

The amount of alkylammonium or pyridinium salt catalyst employed is typically within the range of about 0.1 to 25 mole percent based on the amount of aliphatic diol used. Preferably, the amount used is within the range of about 0.5 to 5.0 mole percent. The amount of catalyst required will vary depending upon which diol is used, temperature, reaction time, and other variables.

The process of the invention may be performed at any desired temperature. The reaction is preferably performed at a temperature within the range of about 0° C. to 220° C. More preferably, the range is about 65° C. to 150° C. At temperatures below about 0° C., the reaction is ordinarily too slow to be useful. Undesirable side reactions or polymerization may occur at temperatures greater than about 220° C. Ordinarily, the reaction temperature will be high enough to permit removal of volatile alcohol or phenolic by-products by distillation.

The process of the invention may be performed at pressures less than, greater than, or equal to atmospheric pressure. Reaction at sub-atmospheric pressure may be used to facilitate removal of alcohol or phenolic by-products, especially ones that are relatively nonvolatile.

Ordinarily, the alkylammonium or pyridinium salt, diol, and diester of carbonic acid are combined and heated with agitation in a suitable reaction vessel. The order in which the reagents are combined is not critical. Usually, the diol and diester of carbonic acid are used in approximately equimolar amounts, although an excess of either may be utilized. It is preferred to use an excess of the acyclic carbonate, generally from 1 to 5 moles of carbonate per mole of glycol. The carbonate may also function as the reaction solvent. The reaction vessel may be constructed of any suitable material, including glass or metal. Preferably, the reaction mixture is agitated in some way, such as by mechanical or magnetic stirring. The process of the invention may be performed batchwise or continuously, as desired.

The reaction is preferably performed in a dry, inert atmosphere to prevent undesirable hydrolysis or oxidation reactions. Suitable inert gases include nitrogen, argon, and the like.

The reaction may be performed without any solvent present if desired, or an inert organic solvent may be used. Examples of suitable inert organic solvents include, but are not limited to, aliphatic and aromatic hydrocarbons, certain halogenated hydrocarbons (for example, dichloromethane and dichloroethane), ethers, amides, and the like, and mixtures thereof.

The reaction products, including the desired cyclic carbonate, alcohol or phenolic by-products, and any unreacted starting materials, may be separated by any suitable means. A preferred method for isolating volatile cyclic carbonates is distillation. The distillation may be performed at atmospheric pressure, or more preferably under vacuum. Nonvolatile carbonates may be isolated by any other suitable purification means, including column chromatography, recrystallization, selective solvent extraction, and the like.

In a preferred process of the invention, ethylene carbonate or propylene carbonate is prepared by heating ethylene glycol or propylene glycol with a diester of carbonic acid in the presence of an alkylammonium or pyridinium salt at a temperature within the range of about 65° C. to 220° C. for a time sufficient to form either ethylene carbonate or propylene carbonate.

In addition to alkylammonium and pyridinium salts, I have also found that tertiary amines and strong or weak-base ion-exchange resins containing active groups selected from alkylammonium or tertiary amino are effective catalysts for the transcarbonation process. The diols and carbonate diesters useful in these embodiments of the invention are the same as those described hereinabove. The reaction parameters and ranges useful for practicing the invention with alkylammonium or pyridinium catalysts also apply to the process catalyzed by tertiary amines or ion-exchange resins containing tertiary amino or alkylammonium groups.

The tertiary amines useful in the process of the invention include all aliphatic and aromatic trisubstituted amines that have a lone pair of electrons. More specifically, the tertiary amines are represented by the formula:

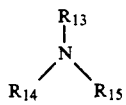

wherein $R_{13}$ to $R_{15}$, which may be the same or different, are selected from the group consisting of alkyl, hydroxyalkyl, aryl, and aralkyl. The groups may be linear, branched, or cyclic, and may contain from 1 to 30 carbon atoms.

Examples of suitable tertiary amines include, but are not limited to, triethylamine, tri-n-propylamine, tri-n-butylamine, methyl diethylamine, N,N'-dimethylcyclohexylamine, pyridine, N,N-dimethylethanolamine, N,N-diethylpropanolamine, and the like, and mixtures thereof. A particularly preferred tertiary amine is triethylamine.

The amount of tertiary amine useful in the process of the invention is typically within the range of about 0.1 to 25 mole percent based on the amount of 1,2- or 1,3-diol used. Preferably, this range is about 1.0 to 5.0 mole percent.

The tertiary amine may be advantageously removed from the reaction mixture by distillation if a volatile amine such as triethylamine is used.

benzene with a tertiary amine such as trimethylamine or dimethylethanolamine. Examples of commercially available resins in this category include "AMBERLITE IRA-400(Cl)" and "AMBERLITE IRA-400(OH)" (Rohm and Haas Co.), and "DOWEX 1X2-100" (Dow Chemical Co.) ion exchange resins. The weak-base resins are typically amine derivatives of chloromethylated polystyrene, condensation products of epichlorohydrin with secondary or tertiary amines, or aminated condensation products of phenol and formaldehyde. Examples of commercially available resins in this category include "AMBERLITE IRA-93" and "DUOLITE A-75" (Rohm and Haas Co.) ion exchange resins.

The amount of ion-exchange resin useful in the process of the invention is typically within the range of about 1.0 to 50 weight percent based on the amount of 1,2- or 1,3-diol used. Preferably, this range is about 10 to 30 weight percent.

The use of tertiary amines, alkylammonium or pyridinium salts, or ion-exchange resins that contain alkylammonium or tertiary amino groups as catalysts often results in improved selectivity to the cyclic carbonate monomer relative to selectivities possible with conventional alkoxide or transition metal catalysts.

The major reaction products when a catalyst of the invention is used are the desired cyclic carbonate and two intermediate products, the acyclic diol monocarbonate and the acyclic diol bis-carbonate. The mono and bis-carbonates can be converted into the desired cyclic carbonate, by distilling the reaction mixture in the presence of the catalyst to remove the alcohol by-products. For example, 2-methyl-1,3-propanediol reacts with dimethyl carbonate to give the three products illustrated below.

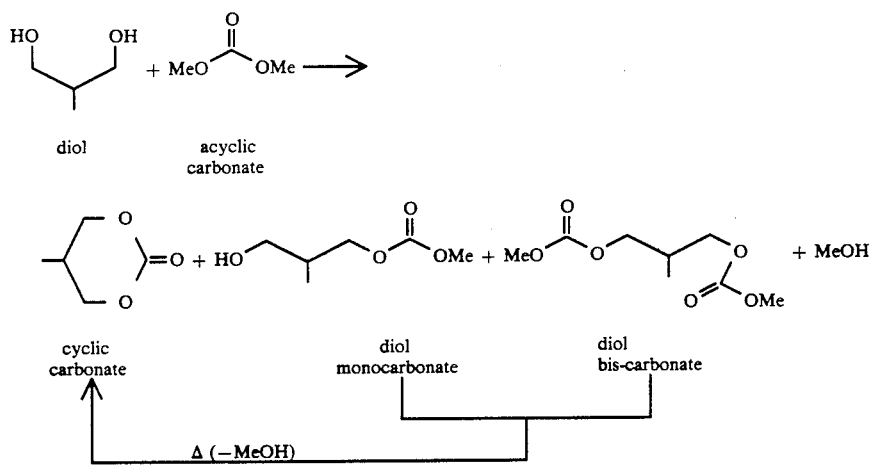

In a preferred process of the invention, ethylene carbonate or propylene carbonate is prepared by heating ethylene glycol or propylene glycol with a diester of carbonic acid in the presence of a tertiary amine at a temperature within the range of about 30° C. to 220° C. for a time sufficient to form either ethylene carbonate or propylene carbonate.

The ion exchange resins useful in the process of the invention are strong and weak-base anionic exchange resins that contain active groups selected from alkylammonium and tertiary amino. The strong-base resins are typically quaternary ammonium derivatives of styrene/divinylbenzene copolymers, which are produced from the reaction of chloromethylated styrene/divinyl- Excellent yields of the cyclic carbonate may be achieved when the reaction mixture is distilled, as illustrated in Example 1. No reaction occurs in the absence of a catalyst (Comparative Example 3).

Interestingly, some of the alkylammonium catalysts appear to require an induction period before they become active catalysts in the process of the invention. Examples 16 and 17 (Table 2) illustrate this point with triethylamine hydrochloride as the catalyst. Although no conversion was observed after 4 hours at 120° C., a 90% conversion was achieved after 20 hours at the same temperature.

Ion-exchange resins that contain alkylammonium or tertiary amino groups can be used as catalysts in the process of the invention, as shown by Example 18 (Table 2) wherein "AMBERLITE" IR-400 (Cl) was used.

Excellent selectivity to propylene carbonate was observed with almost all of the catalysts tried (Tables 2, 3).

As indicated in Table 3, attempts to prepare 7- or 8-membered cyclic carbonates using the process of the invention were not successful (Comparative Examples 25-28). Neither 1,4-butanediol nor 3-methyl-1,5-pentanediol formed any cyclic carbonate.

The examples are meant only to illustrate the invention. Those skilled in the art will recognize many variations that are within the spirit and scope of the invention.

EXAMPLE 1

Preparation of 1,2-Propanediol Cyclic Carbonate (Propylene Carbonate)

A thick-walled glass tube equipped with magnetic stir bar was purged with nitrogen, then charged with propylene glycol (80 g, 1.05 mol), dimethyl carbonate (120 g, 1.33 mol), and tetra-n-butylammonium bromide (3.4 g, 0.010 mol), and sealed. The reaction mixture was heated at 120° C. for 6 hours. The contents of the tube were transferred to a 500-mL round-bottom flask, and methanol was removed by distillation at atmospheric pressure. Gas chromatographic (GC) analysis of the reaction mixture indicated about 92% conversion of the glycol to the corresponding carbonate. To obtain complete conversion of the glycol, dimethyl carbonate (20 g, 0.22 mol) was added to the reaction mixture, which was then heated to vigorous reflux for 1 hour. Methanol was removed by distillation at atmospheric pressure. The residue was purified by vacuum distillation at 0.5 torr. The fractions boiling at 74°-75° C. gave 101 g of >99% pure propylene carbonate (94% yield based on the amount of propylene glycol charged).

EXAMPLE 2

1- Preparation of 2-Methyl-1,3-propanediol Cyclic Carbonate Triethylamine catalyst A thick-walled glass tube equipped with magnetic stir bar was purged with nitrogen, then charged with 2-methyl-1,3-propanediol (36 g, 0.40 mol), dimethyl carbonate (72 g, 0.80 mol), and triethylamine (0.40 g, 0.0040 mol), and sealed. The reaction mixture was heated for 6 hours at 120° C. Gas chromatographic analysis indicated about 90% conversion of the diol to products. The reaction mixture was transferred to a 250-mL round-bottom flask, and methanol was removed by distillation at atmospheric pressure. GC analysis of the reaction mixture showed complete conversion of the diol to products. Vacuum distillation (1 torr) of the residue gave 36.5 g (78% yield based on 2-methyl-1,3-propanediol) of 98% pure 2-methyl-1,3-propanediol cyclic carbonate.

EXAMPLES 3-28

Preparation of Cyclic Carbonates by Transesterification Using Alkylammonium Catalysts A thick-walled glass tube equipped with a teflon-screw stopcock and a magnetic stir bar was used as the reaction vessel. The tube was charged with diol (0.22 mol), acyclic carbonate (0.44 mol), and alkylammonium catalyst (0.0022 mol). The headspace above the liquids was purged with nitrogen, the tube was closed, and the reaction was performed under the temperature/time conditions listed in Tables 1-3. The percent conversion of diol and relative ratios (area percent) of cyclic carbonate, diol monocarbonate, and diol bis-carbonate products were determined by gas chromatography (Tables 1-3) following cooling of the reaction mixture to 23° C.

EXAMPLES 29-39

Preparation of Cyclic Carbonates by Transesterification Using Tertiary Amine Catalysts The procedure of Examples 3-28 was followed, except that a tertiary amine catalyst was used in each case. The results appear in Table 4.

TABLE 1.

PREPARATION OF MPD CYCLIC CARBONATE BY TRANSESTERIFICATION USING ALKYLAMMONIUM CATALYSTS

| EX # | DIOL | Acyclic Carbonate | Cat. | Temp °C. | Time Hr. | % Conv. | % Cyclic Carbonate | % Diol Monocarbonate | % Diol Bis-Carbonate |
|---|---|---|---|---|---|---|---|---|---|
| C-3 | MPD | DMC | — | 120 | 16 | 0 | 0 | 0 | 0 |
| 4 | MPD | DMC | TBAB | 120 | 16 | 97 | 53 | 14 | 30 |
| 5 | MPD | DMC | TBAI | 120 | 16 | 89 | 37 | 32 | 31 |
| 6 | MPD | DMC | PyrMI | 120 | 16 | 80 | 3 | 70 | 27 |
| 7 | MPD | DMC | TBAH | 120 | 2 | 77 | 60 | 29 | 11 |
| 8 | MPD | DMC | TBAHS | 120 | 16 | 5 | 49 | 51 | 0 |
| 9 | MPD | DMC | TBAB | 80 | 6 | 12 | 33 | 59 | 8 |
| 10 | MPD | DPC | TBAB | 120 | 16 | 92 | 72 | 20 | 8 |
| 11 | MPD | DMC | TBADHP | 120 | 20 | 89 | 7 | 67 | 26 |

C = comparative example
MPD = 2-methyl-1,3-propanediol
DMC = dimethyl carbonate; DPC = diphenyl carbonate
TBAB = tetra-n-butylammonium bromide; TBAI = tetra-n-butylammonium iodide;
PyrMI = pyridinium methyl iodide; TBAH = tetra-n-butylammonium hydroxide;
TBAHS = tetra-n-butylammonium hydrogen sulfate
TBADHP = tetra-n-butylammonium dihydrogen phosphate

TABLE 2.

PREPARATION OF PROPYLENE CARBONATE BY TRANSESTERIFICATION USING ALKYLAMMONIUM CATALYSTS

| EX # | DIOL | Acyclic Carbonate | Cat. | Temp °C. | Time Hr. | % Conv. | % Cyclic Carbonate | % Diol Monocarbonate | % Diol Bis-Carbonate |
|---|---|---|---|---|---|---|---|---|---|
| C-12 | PG | DMC | — | 120 | 4 | 0 | 0 | 0 | 0 |
| 13 | PG | DMC | TBAB | 120 | 4 | 98 | 100 | 0 | 0 |
| 14 | PG | DMC | TBAB | 100 | 6 | 60 | 100 | 0 | 0 |
| 15 | PG | DMC | TBAC | 120 | 4 | 87 | 99 | 0 | 1 |
| 16 | PG | DMC | TEAHC | 120 | 4 | 0 | 0 | 0 | 0 |
| 17 | PG | DMC | TEAHC | 120 | 20 | 90 | 99 | 0 | 1 |
| 18 | PG | DMC | AMBC* | 120 | 20 | 53 | 99 | 0 | 1 |
| 19 | PG | DEC | TBAB | 120 | 20 | 4 | 66 | 0 | 34 |
| 20 | PG | DEC | TBAH | 120 | 40 | 23 | 96 | 0 | 4 |

C = comparative example
PG = propylene glycol
DMC = dimethyl carbonate; DEC = diethyl carbonate
TBAB = tetra-n-butylammonium bromide; TBAC = tetra-n-butylammonium chloride;
TEAHC = triethylamine hydrochloride; AMBC = "AMBERLITE" IR-400 (Cl) ion-exchange resin;
TBAH = tetra-n-butylammonium hydroxide
*25 weight percent AMBC resin used based on the amount of PG

TABLE 3.

PREPARATION OF CYCLIC CARBONATES BY TRANSESTERIFICATION USING ALKYLAMMONIUM CATALYSTS

| EX # | DIOL | Acyclic Carbonate | Cat. | Temp °C. | Time Hr. | % Conv. | % Cyclic Carbonate | % Diol Monocarbonate | % Diol Bis-Carbonate |
|---|---|---|---|---|---|---|---|---|---|
| 21 | EG | DMC | TBAB | 120 | 4 | 83 | 62 | 34 | 4 |
| 22 | EG | DMC | TBAB | 120 | 6 | 83 | 63 | 33 | 4 |
| 23 | PD | DMC | TBAB | 120 | 6 | 87 | 65 | 1 | 34 |
| 24 | GLY | DMC | TBAB | 120 | 6 | 92 | 92* | 0 | 8** |
| C-25 | BD | DMC | TBAB | 120 | 16 | 91 | 0 | 44 | 56 |
| C-26 | BD | DPC | TBAB | 120 | 16 | 5 | 0 | 0 | 0 |
| C-27 | BD | DMC | PyrMI | 120 | 16 | 89 | 0 | 66 | 34 |
| C-28 | MPND | DMC | TBAB | 120 | 6 | 76 | 0 | 78 | 22 |

C = comparative example
EG = ethylene glycol; PD = 1,3-propanediol; BD = 1,4-butanediol; GLY = glycerin
MPND = 3-methyl-1,5-pentanediol
DMC = dimethyl carbonate; DPC = diphenyl carbonate
TBAB = tetra-n-butylammonium bromide; PyrMI = pyridinium methyl iodide
*Major product was 5-membered cyclic carbonate
**Methyl (2-oxo-1,3-dioxolan-4-yl)methyl carbonate [76913-26-6]

TABLE 4.

PREPARATION OF CYCLIC CARBONATES BY TRANSESTERIFICATION USING TERTIARY AMINE CATALYSTS

| EX # | DIOL | Acyclic Carbonate | Cat. | Temp °C. | Time Hr. | % Conv. | % Cyclic Carbonate | % Diol Monocarbonate | % Diol Bis-Carbonate |
|---|---|---|---|---|---|---|---|---|---|
| 29 | MPD | DMC | TBAM | 120 | 16 | 96 | 60 | 17 | 23 |
| 30 | MPD | DMC | TEA | 120 | 16 | 99 | 71 | 10 | 19 |
| 31 | MPD | DMC | Pyr | 120 | 12 | 78 | 32 | 44 | 24 |
| 32 | MPD | DMC | TEA | 150 | 6 | 90 | 72 | 20 | 9 |
| 33 | MPD | DMC | TEA | 120 | 6 | 87 | 70 | 20 | 10 |
| 34 | MPD | DMC | TEA | 100 | 6 | 84 | 63 | 24 | 13 |
| 35 | MPD | DMC | TEA | 80 | 6 | 58 | 67 | 30 | 3 |
| 36 | PG | DMC | Pyr | 120 | 12 | 93 | 100 | 0 | 0 |
| 37 | EG | DMC | TEA | 120 | 4 | 81 | 83 | 13 | 4 |
| 38 | EG | DMC | TEA | 120 | 6 | 84 | 63 | 33 | 4 |
| 39 | DBD | DMC | TEA* | 120 | 16 | 10 | 97 | 1 | 2 |

MPD = 2-methyl-1,3-propanediol; PG = propylene glycol; EG = ethylene glycol;
DBD = 2,3-dimethyl-2,3-butanediol (pinacol)
DMC = dimethyl carbonate
TBAM = tri-n-butylamine; TEA = triethylamine; Pyr = pyridine
*0.011 moles of catalyst used (5 times the normal amount).

I claim:

1. A process for preparing a 5- or 6-membered cyclic carbonate comprising: reacting a 1,2- or 1,3-diol with a diester of carbonic acid in the presence of an alkylammonium or a pyridinium salt at a temperature and for a time sufficient to form the cyclic carbonate.

2. The process of claim 1 wherein the aliphatic 1,2- or 1,3-diol has the formula:

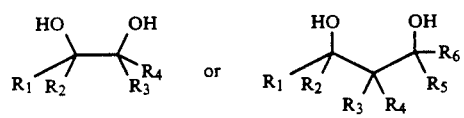

wherein $R_1$ through $R_6$, which may be the same or different, represent alkyl, hydroxyalkyl, cycloalkyl, aryl, or aralkyl groups, and wherein any pair of said $R_1$ through $R_6$ groups may represent a cycloalkyl group.

3. The process of claim 1 wherein the 1,2- or 1,3-diol is selected from the group consisting of ethylene glycol, propylene glycol, 1,3-propanediol, 2-methyl-1,3-propanediol, pinacol, glycerin, and 2,2-dimethyl-1,3-propanediol.

4. The process of claim 1 wherein the diester of carbonic acid has the formula:

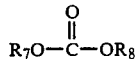

wherein $R_7$ and $R_8$, which may be the same or different, represent alkyl, aryl, or aralkyl groups.

5. The process of claim 1 wherein the diester of carbonic acid is selected from the group consisting of dimethyl carbonate, diethyl carbonate, and diphenyl carbonate.

6. The process of claim 1 wherein the alkylammonium salt has the formula:

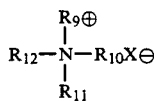

wherein $R_9$ through $R_{12}$, which may be the same or different, are selected from the group consisting of hydrogen, alkyl, hydroxyalkyl, aryl, and aralkyl, and only one of said $R_9$ through $R_{12}$ groups may be hydrogen; and wherein X- is a monovalent anion selected from the group consisting of halide, carbonate, bicarbonate, hydroxide, alkoxide, dihydrogen phosphate, and bisulfate.

7. The process of claim 1 wherein the alkylammonium or pyridinium salt is selected from the group consisting of tri-n-butylamine hydrochloride, trimethylamine hydrochloride, tetra-n-butylammonium bromide, tetra-n-butylammonium chloride, trimethyl-(2-hydroxyethyl)ammonium chloride, tetraethylammonium iodide, tetra-n-butylammonium hydroxide, pyridinium methyl iodide, pyridine hydrochloride, and tetramethylammonium bromide.

8. The process of claim 1 wherein the temperature is within the range of about 0° C. to 220° C.

9. The process of claim 1 wherein alcohol or phenolic by-products generated in the reaction are removed from the desired cyclic carbonate by distillation.

10. The process of claim 1 wherein the cyclic carbonate is purified by distillation in the presence of the alkylammonium or pyridinium salt.

11. A process for preparing a 5- or 6-membered cyclic carbonate comprising: reacting a diol selected from the group consisting of ethylene glycol, propylene glycol, 2-methyl-1,3-propanediol, pinacol, glycerin, and 2,2-dimethyl-1,3-propanediol with a diester of carbonic acid in the presence of an alkylammonium or a pyridinium salt at a temperature within the range of about 0° C. to 220° C. for a time sufficient to form the cyclic carbonate.

12. The process of claim 11 wherein the diester of carbonic acid is selected from the group consisting of dimethyl carbonate, diethyl carbonate, and diphenyl carbonate.

13. The process of claim 11 wherein the alkylammonium or pyridinium salt is selected from the group consisting of tri-n-butylamine hydrochloride, trimethylamine hydrochloride, tetra-n-butylammonium bromide, tetra-n-butylammonium chloride, tetraethylammonium iodide, tetra-n-butylammonium hydroxide, pyridinium methyl iodide, pyridine hydrochloride, and tetramethylammonium bromide.

14. A process for preparing ethylene carbonate comprising: reacting ethylene glycol with a diester of carbonic acid in the presence of an alkylammonium or a pyridinium salt at a temperature within the range of about 0° C. to 220° C. for a time sufficient to form ethylene carbonate.

15. The process of claim 14 wherein the diester of carbonic acid is selected from the group consisting of dimethyl carbonate, diethyl carbonate, and diphenyl carbonate.

16. The process of claim 14 wherein the alkylammonium or pyridinium salt is selected from the group consisting of tri-n-butylamine hydrochloride, trimethylamine hydrochloride, tetra-n-butylammonium bromide, tetra-n-butylammonium chloride, tetraethylammonium iodide, tetra-n-butylammonium hydroxide, pyridinium methyl iodide, pyridine hydrochloride, and tetramethylammonium bromide.

17. A process for preparing propylene carbonate comprising: reacting propylene glycol with a diester of carbonic acid in the presence of an alkylammonium or a pyridinium salt at a temperature within the range of about 0° C. to 220° C. for a time sufficient to form propylene carbonate.

18. The process of claim 17 wherein the diester of carbonic acid is selected from the group consisting of dimethyl carbonate, diethyl carbonate, and diphenyl carbonate.

19. The process of claim 17 wherein the alkylammonium or pyridinium salt is selected from the group consisting of tri-n-butylamine hydrochloride, trimethylamine hydrochloride, tetra-n-, butylammonium bromide, tetra-n-butylammonium chloride, tetraethylammonium iodide, tetra-n-butylammonium hydroxide, pyridinium methyl iodide, pyridine hydrochloride, and tetramethylammonium bromide.

20. A process for preparing a 5- or 6-membered cyclic carbonate comprising: reacting a 1,2- or 1,3-diol with a diester of carbonic acid in the presence of a tertiary amine at a temperature and for a time sufficient to form the cyclic carbonate.

21. The process of claim 20 wherein the tertiary amine has the formula:

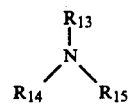

wherein $R_{13}$ to $R_{15}$, which may be the same or different, are selected from the group consisting of $C_1$ to $C_{30}$ alkyl, hydroxyalkyl, aryl, and aralkyl groups.

22. The process of claim 20 wherein the tertiary amine is selected from the group consisting of trimethylamine, triethylamine, tributylamine, N,N'-dimethylcyclohexylamine, N,N-dimethylethanolamine, and pyridine.

23. The process of claim 20 wherein the reaction is performed at a temperature within the range of about 0° C. to 220° C.

24. The process of claim 20 wherein the diester of carbonic acid is selected from the group consisting of dimethyl carbonate, diethyl carbonate, and diphenyl carbonate.

25. The process of claim 20 wherein the aliphatic 1,2- or 1,3-diol is selected from the group consisting of ethylene glycol, propylene glycol, 1,3-propanediol, 2-methyl-1,3-propanediol, pinacol, glycerin, and 2,2-dimethyl-1,3-propanediol.

26. A process for preparing a 5- or 6-membered cyclic carbonate comprising: reacting 1,2- or 1,3-diol with an acyclic diester of carbonic acid in the presence of a strong or weak-base ion-exchange resin containing active groups selected from alkylammonium or tertiary amino, at a temperature and for a time sufficient to form the cyclic carbonate.

27. The process of claim 26 wherein the reaction is performed at a temperature within the range of about 0° C. to 220° C.

28. The process of claim 26 wherein the diester of carbonic acid is selected from the group consisting of dimethyl carbonate, diethyl carbonate, and diphenyl carbonate.

29. The process of claim 26 wherein the 1,2- or 1,3-diol is selected from the group consisting of ethylene glycol, propylene glycol, 1,3-propanediol, 2-methyl-1,3-propanediol, pinacol, glycerin, and 2,2-dimethyl-1,3-propanediol.

30. The process of claim 26 wherein the ion-exchange resin is a strong-base resin that contains an active alkylammonium group selected from trimethylammonium chloride and dimethyl-(2-hydroxyethyl)ammonium chloride.

31. The process of claim 26 wherein the ion-exchange resin is a weak-base resin that contains an active tertiary amine group selected from dimethylamino, diethylamino, and di-n-butylamino.

* * * * *